(12) United States Patent
Kohl et al.

(10) Patent No.: US 11,430,123 B2
(45) Date of Patent: Aug. 30, 2022

(54) SAMPLING LATENT VARIABLES TO GENERATE MULTIPLE SEGMENTATIONS OF AN IMAGE

(71) Applicant: DeepMind Technologies Limited, London (GB)

(72) Inventors: Simon Kohl, London (GB); Bernardino Romera-Paredes, London (GB); Danilo Jimenez Rezende, London (GB); Seyed Mohammadali Eslami, London (GB); Pushmeet Kohli, London (GB); Andrew Zisserman, London (GB); Olaf Ronneberger, London (GB)

(73) Assignee: DeepMind Technologies Limited, London (GB)

( * ) Notice: Subject to any disclaimer, the term of this patent is extended or adjusted under 35 U.S.C. 154(b) by 109 days.

(21) Appl. No.: 16/881,775

(22) Filed: May 22, 2020

(65) Prior Publication Data
US 2020/0372654 A1    Nov. 26, 2020

Related U.S. Application Data

(60) Provisional application No. 62/852,178, filed on May 23, 2019.

(51) Int. Cl.
*G06T 7/10* (2017.01)
*A61B 5/00* (2006.01)
*G06T 7/00* (2017.01)

(52) U.S. Cl.
CPC .............. *G06T 7/10* (2017.01); *A61B 5/0033* (2013.01); *A61B 5/7264* (2013.01);
(Continued)

(58) Field of Classification Search
CPC ..... A61B 5/0033; A61B 5/055; A61B 5/7264; G06T 7/0012; G06T 7/10; G06T 7/11;
(Continued)

(56) References Cited

U.S. PATENT DOCUMENTS 10,482,603 B1 *  11/2019  Fu ........................... G06F 17/15
10,872,275 B2 *  12/2020  Wang ................... G06N 3/0454
(Continued)

OTHER PUBLICATIONS

Chartsias et al., "Factorised Representation Learning in Cardiac Image Analysis," CoRR, Mar. 2019, https://128.84.21.199/abs/1903.09467v1, 18 pages.
(Continued)

*Primary Examiner* — Katrina R Fujita
(74) *Attorney, Agent, or Firm* — Fish & Richardson P.C.

(57) ABSTRACT

Methods, systems, and apparatus, including computer programs encoded on a computer storage medium, for generating a plurality of possible segmentations of an image. In one aspect, a method comprises: receiving a request to generate a plurality of possible segmentations of an image; sampling a plurality of latent variables from a latent space, wherein each latent variable is sampled from the latent space in accordance with a respective probability distribution over the latent space that is determined based on the image; generating a plurality of possible segmentations of the image, comprising, for each latent variable, processing the image and the latent variable using a segmentation neural network having a plurality of segmentation neural network parameters to generate the possible segmentation of the image; and providing the plurality of possible segmentations of the image in response to the request.

28 Claims, 7 Drawing Sheets

TRAINING SYSTEM
(HIERARCHICAL LATENT VARIABLE)
350

(52) U.S. Cl.
CPC .. *G06T 7/0012* (2013.01); *G06T 2207/20112* (2013.01); *G06T 2207/30004* (2013.01)

(58) Field of Classification Search
CPC . G06T 2207/10056; G06T 2207/10072; G06T 2207/10116; G06T 2207/10132; G06T 2207/20016; G06T 2207/20084; G06T 2207/20112; G06T 2207/30004; G06T 2207/30096
See application file for complete search history.

(56) References Cited

U.S. PATENT DOCUMENTS

| | | | |
|---|---|---|---|
| 11,062,229 B1* | 7/2021 | Mnih | G06F 17/11 |
| 2016/0283858 A1* | 9/2016 | Lin | G06K 9/629 |
| 2018/0101784 A1* | 4/2018 | Rolfe | G06K 9/00986 |
| 2019/0046068 A1* | 2/2019 | Ceccaldi | G06K 9/6271 |
| 2020/0125852 A1* | 4/2020 | Carreira | G06K 9/00718 |
| 2020/0364852 A1* | 11/2020 | Park | G06T 7/174 |
| 2020/0401916 A1* | 12/2020 | Rolfe | G06N 5/04 |
| 2021/0382497 A1* | 12/2021 | Zhi | G06T 7/55 |

OTHER PUBLICATIONS

PCT International Search Report and Written in Opinion in International Appln. No. PCT/EP2020/064069, dated Aug. 18, 2020, 14 pages.
Arganda-Carreras et al., "Crowdsourcing the creation of image segmentation algorithms for connectomics," Frontiers in Neuroanatomy, Nov. 2015, 13 pages.
Armato et al., "The Lung Image Database Consortium (LIDC) and Image Database Resource Initiative (IDRI): A Completed Reference Database of Lung Nodules on CT Scans," Medical Physics, Jan. 2011, 38(2):915-931.
Batra et al., "Diverse M-Best Solutions in Markov Random Fields," European Conference on Computer Vision, 2012, 16 pages.
Bellemare et al., "The Cramer Distance as a Solution to Biased Wasserstein Gradients," https://arxiv.org/abs/1705.10743, May 2017, 20 pages.
Bouchacourt et al., "DISCO Nets : Dissimilarity Coefficients Networks," Advances in Neural Information Processing Systems 29 (NIPS 2016), Dec. 2016, 9 pages.
Chen et al., "Computing the M Most Probable Modes of a Graphical Model," Artificial Intelligence and Statistics, 2013, 161-169.
Chen et al., "TensorMask: A Foundation for Dense Object Segmentation," https://arxiv.org/abs/1903.12174v1, Mar. 2019, 12 pages.
Clark et al., "The Cancer Imaging Archive (TCIA): Maintaining and Operating a Public Information Repository," Journal of Digital Imaging, Jul. 2013, 13 pages.
Cordts et al., "The Cityscapes Dataset for Semantic Urban Scene Understanding," 2016 IEEE Conference on Computer Vision and Pattern Recognition (CVPR), Jun. 2016, 3213-3223.
De Fauw et al., "Clinically applicable deep learning for diagnosis and referral in retinal disease," Nature Medicine, Aug. 2018, 15 pages.
De Fauw et al., "Hierarchical Autoregressive Image Models with Auxiliary Decoders," https://arxiv.org/abs/1903.04933, Mar. 2019, 32 pages.
Esser et al., "A Variational U-Net for Conditional Appearance and Shape Generation," 2018 IEEE/CVF Conference on Computer Vision and Pattern Recognition, Jun. 2018, 8857-8866.
Goodfellow, "NIPS 2016 Tutorial: Generative Adversarial Networks," https://arxiv.org/abs/1701.00160v1, Dec. 2016, 57 pages.
Gregor et al., "Towards Conceptual Compression," Advances in Neural Information Processing Systems 29 (NIPS 2016), 2016, 9 pages.
Guzman-Rivera et al., "Multiple Choice Learning: Learning to Produce Multiple Structured Outputs," Advances in Neural Information Processing Systems 25 (NIPS 2012), 2012, 9 pages.

He et al., "Identity Mappings in Deep Residual Networks," European Conference on Computer Vision, Sep. 2016, 630-645.
He et al., "Mask R-CNN," 2017 IEEE International Conference on Computer Vision (ICCV), Oct. 2017, 2980-2988.
Higgins et al., "beta-VAE: Learning Basic Visual Concepts with a Constrained Variational Framework," International Conference on Learning Representations, retrieved from URL <https://pdfs.semanticscholar.org/a902/26c41b79f8b06007609f39f82757073641e2.pdf>, 2017, 13 pages.
Ilg et al., "Uncertainty Estimates for Optical Flow with Multi-Hypotheses Networks," https://arxiv.org/abs/1802.07095v1, Feb. 2018, 19 pages.
Isola et al., "Image-to-Image Translation with Conditional Adversarial Networks," https://arxiv.org/abs/1611.07004v2, Nov. 2017, 17 pages.
Jang et al., "Categorical Reparameterization with Gumbel-Softmax," https://arxiv.org/abs/1611.01144v1, Nov. 2016, 13 pages.
Jimenez Rezende et al., "Stochastic Backpropagation and Approximate Inference in Deep Generative Models,"Proceedings of the 31st International Conference on Machine Learning, 2014, 9 pages.
Kasthuri et al., "Saturated Reconstruction of a Volume of Neocortex," Cell, Jul. 2015, 162(3):648-661.
Kendall et al., "Bayesian SegNet: Model Uncertainty in Deep Convolutional Encoder-Decoder Architectures for Scene Understanding," https://arxiv.org/abs/1511.02680v1, Nov. 2015, 9 pages.
Kendall et al., "What Uncertainties Do We Need in Bayesian Deep Learning for Computer Vision?," Advances in Neural Information Processing Systems 30 (NIPS 2017), 2017, 11 pages.
Kingma et al., "Adam: A Method for Stochastic Optimization," https://arxiv.org/abs/1412.6980v1, Dec. 2014, 9 pages.
Kingma et al., "Auto-Encoding Variational Bayes," https://arxiv.org/abs/1312.6114v4, Dec. 2013, 14 pages.
Kingma et al., "Improving Variational Inference with Inverse Autoregressive Flow," https://arxiv.org/abs/1606.04934v1, Jun. 2016, 10 pages.
Kingma et al., "Semi-supervised Learning with Deep Generative Models," Advances in Neural Information Processing Systems 27 (NIPS 2014), 2014, 9 pages.
Kirillov et al., "Inferring M-Best Diverse Labelings in a Single One," 2015 IEEE International Conference on Computer Vision (ICCV), Dec. 2015, 1814-1822.
Kirillov et al., "Joint M-Best-Diverse Labelings as a Parametric Submodular Minimization," Advances in Neural Information Processing Systems 29 (NIPS 2016), 2016, 9 pages.
Kirillov et al., "M-Best-Diverse Labelings for Submodular Energies and Beyond," Advances in Neural Information Processing Systems 28 (NIPS 2015), 2015, 9 pp. 613-621.
Kirillov et al., "Panoptic Segmentation," https://arxiv.org/abs/1801.00868v1, Jan. 2018, 9 pages.
Klebanov, "N-distances and their Applications," Charles University in Prague, retrieved from URL <https://www.researchgate.net/profile/Lev_Klebanov/publication/40369195_N-distances and their applications/links/54f397ee0cf2f9e34f07e64f/N-distances-and-their-applications.pdf>, 2005, 91 pages.
Kohl et al., "A Hierarchical Probabilistic U-Net for Modeling Multi-Scale Ambiguities," https://arxiv.org/abs/1905.13077, May 2019, 25 pages.
Kohl et al., "A Probabilistic U-Net for Segmentation of Ambiguous Images, 32nd Conference on Neural Information Processing Systems (NeurIPS 2018), retrieved from URL <http://papers.nips.cc/paper/7928-a-probabilistic-u-net-for-segmentation-of-ambiguous-images.pdf," 2018, 11 pages.
Kosub, "A note on the triangle inequality for the Jaccard distance," https://arxiv.org/abs/1612.02696, Dec. 2016, 5 pages.
Kuhn, "The Hungarian Method for the Assignment Problem," Naval Research Logistics (NRL), 1955, 83-97.
Kulikov et al., "Instance Segmentation by Deep Coloring," https://arxiv.org/abs/1807.10007, Jul. 2018, 10 pages.
Kulikov et al., "Instance Segmentation of Biological Images Using Harmonic Embeddings," https://arxiv.org/abs/1904.05257v1, Apr. 2019, 9 pages.
Lakshminarayanan et al., "Simple and Scalable Predictive Uncertainty Estimation using Deep Ensembles," Advances in Neural Information Processing Systems 30 (NIPS 2017), 2017, 12 pages.

(56) References Cited

OTHER PUBLICATIONS

Lee et al., "Stochastic Multiple Choice Learning for Training Diverse Deep Ensembles," Advances in Neural Information Processing Systems 29 (NIPS 2016), 2016, 9 pages.

Lee et al., "Superhuman Accuracy on the SNEMI3D Connectomics Challenge," https://arxiv.org/abs/1706.00120, May 2017, 11 pages.

Lee et al., "Why M Heads are Better than One: Training a Diverse Ensemble of Deep Networks," https://arxiv.org/abs/1511.06314, Nov. 2015, 18 pages.

Lin et al., "Focal Loss for Dense Object Detection," 2017 IEEE International Conference on Computer Vision (ICCV), Oct. 2017, 2999-3007.

Lipkus, "A proof of the triangle inequality for the Tanimoto distance," Journal of Mathematical Chemistry, Oct. 1999, 26(1-3):263-265.

Liu et al., "Unsupervised Image-to-Image Translation Networks," Advances in Neural Information Processing Systems 30 (NIPS 2017), 2017, 9 pages.

Maaløe et al., "BIVA: A Very Deep Hierarchy of Latent Variables for Generative Modeling," https://arxiv.org/abs/1902.02102, Feb. 2019, 25 pages.

Menick et al., "Generating High Fidelity Images with Subscale Pixel Networks and Multidimensional Upscaling," https://arxiv.org/abs/1812.01608, Dec. 2018, 15 pages.

Munkres, "Algorithms for the Assignment and Transportation Problems," Journal of the Society for Industrial and Applied Mathematics, Mar. 1957, 5(1):32-38.

Nalisnick et al., "Do Deep Generative Models Know What They Don't Know?," https://arxiv.org/abs/1810.09136v1, Oct. 2018, 19 pages.

Nikolov et al., "Deep learning to achieve clinically applicable segmentation of head and neck anatomy for radiotherapy," https://arxiv.org/abs/1809.04430, Sep. 2018, 31 pages.

Nunez-Iglesias et al., "Graph-based active learning of agglomeration (GALA): a Python library to segment 2D and 3D neuroimages," Frontiers in Neuroinformatics, Apr. 2014, 8:1-6.

Park et al., "Semantic Image Synthesis with Spatially-Adaptive Normalization," https://arxiv.org/abs/1903.07291v1, Mar. 2019, 19 pages.

Rand, "Objective Criteria for the Evaluation of Clustering Methods," Journal of the American Statistical Association, 1971, 66(336):846-850.

Rao, "Diversity and Dissimilarity Coefficients: A Unified Approach," Theoretical Population Biology, Feb. 1982, 21(1):24-43.

Rezende et al., "Taming VAEs," https://arxiv.org/abs/1810.00597, Oct. 2018, 21 pages.

Ronneberger et al., "U-Net: Convolutional Networks for Biomedical Image Segmentation," https://arxiv.org/abs/1505.04597, May 2015, 8 pages.

Rupprecht et al., "Learning in an Uncertain World: Representing Ambiguity Through Multiple Hypotheses," 2017 IEEE International Conference on Computer Vision (ICCV), Oct. 2017, 3611-3620.

Salimans et al., "Improved Techniques for Training GANs," Advances in Neural Information Processing Systems 29 (NIPS 2016), 2016, 9 pages.

Salimans et al., "Improving GANs Using Optimal Transport," https://arxiv.org/abs/1803.05573, Mar. 2018, 13 pages.

Salimans et al., "PixelCNN++: Improving the PixelCNN with Discretized Logistic Mixture Likelihood and Other Modifications," https://arxiv.org/abs/1701.05517, Jan. 2017, 10 pages.

Sohn et al., "Learning Structured Output Representation using Deep Conditional Generative Models," Advances in Neural Information Processing Systems 28 (NIPS 2015), 2015, 9 pages.

Sonderby et al., "Ladder Variational Autoencoders," Advances in Neural Information Processing Systems 29 (NIPS 2016), 2016, 9 pages.

Székely et al., "Energy statistics: A class of statistics based on distances," Journal of Statistical Planning and Inference, Aug. 2013, 143(8):24 pages.

Wu et al., "Bridging Category-level and Instance-level Semantic Image Segmentation," https://arxiv.org/abs/1605.06885, May 2016, 14 pages.

Xiong et al., "UPSNet: A Unified Panoptic Segmentation Network," https://arxiv.org/abs/1901.03784v1, Jan. 2019, 14 pages.

Zhu et al., "Toward Multimodal Image-to-Image Translation," Advances in Neural Information Processing Systems 30 (NIPS 2017), 2017, 12 pages.

Zhu et al., "Unpaired Image-to-Image Translation Using Cycle-Consistent Adversarial Networks," 2017 IEEE International Conference on Computer Vision (ICCV), Oct. 2017, 2242-2251.

International Preliminary Report on Patentability in International Appln. No. PCT/EP2020/064069. dated Dec. 2, 2021, 8 pages.

* cited by examiner

SAMPLING LATENT VARIABLES TO GENERATE MULTIPLE SEGMENTATIONS OF AN IMAGE

CROSS-REFERENCE TO RELATED APPLICATION

This application claims priority under 35 U.S.C. 119 to Provisional Application No. 62/852,178, filed May 23, 2019, which is incorporated by reference.

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a segmentation system implemented as computer programs on one or more computers in one or more locations that is configured to process an image to generate multiple possible segmentations of the image. Each segmentation may represent a different hypothesis for the ground truth (i.e., actual) segmentation of the image.

According to embodiments there is provided a method performed by one or more data processing apparatus. The method comprises receiving a request to generate a plurality of possible segmentations of an image, sampling a plurality of latent variables from a latent space, wherein each latent variable is sampled from the latent space in accordance with a respective probability distribution over the latent space that is determined based on the image, generating a plurality of possible segmentations of the image, comprising, for each latent variable, processing the image and the latent variable using a segmentation neural network having a plurality of segmentation neural network parameters to generate the possible segmentation of the image and providing the plurality of possible segmentations of the image in response to the request.

In an embodiment sampling the plurality of latent variables from the latent space comprises generating a probability distribution over the latent space based on the image; and sampling each of the plurality of latent variables from the latent space in accordance with the probability distribution.

Generating a probability distribution over the latent space based on the image may comprise processing the image using a prior neural network to generate an output that defines parameters of the probability distribution over the latent space.

The probability distribution may be a Normal probability distribution, and the parameters of the probability distribution include a mean vector and a variance vector.

Processing the image and the latent variable using a segmentation neural network to generate the possible segmentation of the image may comprise processing the image using a first plurality of segmentation neural network layers to generate a feature map and processing the feature map and the latent variable using a second plurality of segmentation neural network layers to generate the possible segmentation of the image.

The segmentation neural network and the prior neural network may have been trained jointly with a posterior neural network configured to, during training, process a training image and a target segmentation of the training image to generate an output that defines parameters of a posterior probability distribution over the latent space.

In an embodiment the latent space comprises a hierarchy of latent sub-spaces and sampling a latent variable from the latent space comprises sampling a respective latent sub-variable from each latent sub-space of the latent space. Sampling a latent sub-variable from a given latent sub-space comprises generating a probability distribution over the given latent sub-space based on: (i) the image, and (ii) latent sub-variables sampled from any latent sub-spaces that precede the given latent sub-space in the hierarchy of latent sub-spaces and sampling the latent sub-variable from the given latent sub-space in accordance with the probability distribution over the given latent sub-space.

For each particular latent sub-space in the hierarchy of latent subspaces, a dimensionality of the particular latent sub-space may be greater than a dimensionality of any latent sub-space that precedes the particular latent sub-space in the hierarchy of latent sub-spaces.

Generating the probability distribution over the first latent sub-space in the hierarchy of latent sub-spaces may comprise processing one or more feature maps derived from the image using one or more neural network layers to generate an output that defines parameters of the probability distribution over the first latent sub-space.

The one or more feature maps may be intermediate outputs of the segmentation neural network.

The one or more neural network layers may be intermediate layers of the segmentation neural network.

The probability distribution over the first latent sub-space is a Normal probability distribution, and the parameters of the probability distribution over the first latent sub-space include a mean vector and a variance vector.

In one embodiment generating the probability distribution over each latent sub-space after the first latent sub-space in the hierarchy of latent sub-spaces comprises processing one or more feature maps derived from the image and a representation of the latent sub-variable sampled from the preceding latent sub-space in the hierarchy of latent subspaces using one or more neural network layers to generate an output that defines parameters of the probability distribution over the latent sub-space.

The representation of the latent sub-variable sampled from the preceding latent sub-space may be an up-scaled representation of the latent sub-variable sampled from the preceding latent sub-space.

The one or more feature maps may be intermediate outputs of the segmentation neural network.

The one or more neural network layers may be intermediate layers of the segmentation neural network.

In an embodiment for each latent sub-space after the first latent sub-space, the probability distribution over the latent sub-space is a Normal probability distribution, and the parameters of the probability distribution over the latent sub-space include a mean vector and a variance vector.

In an embodiment processing the image and the latent variable using a segmentation neural network to generate the possible segmentation of the image comprises providing the image as an input to an input layer of the segmentation neural network and providing each latent sub-variable as an input to a respective intermediate layer of the segmentation neural network.

In an embodiment the segmentation neural network has been trained jointly with a posterior neural network configured to, during training, process a training image and a target segmentation of the training image to generate an output that defines, for each latent sub-space of the hierarchy of latent sub-spaces, parameters of a posterior probability distribution over the latent sub-space.

Each possible segmentation of the image may characterize, for each pixel of the image, a respective likelihood that the pixel is included in each of a plurality of categories.

The image may be a medical image and each of the plurality of categories may correspond to a respective tissue type.

The medical image may be a computed tomography (CT) image.

The segmentation neural network may be a convolutional neural network.

The segmentation neural network may have a U-Net neural network architecture.

In an embodiment there is provided a system comprising one or more computers and one or more storage devices storing instructions that when executed by the one or more computers cause the one or more computers to perform the operations of one or more of the respective methods described hereinbefore.

In an embodiment there is provided one or more computer storage media storing instructions that when executed by one or more computers cause the one or more computers to perform the operations of one or more of the respective methods described hereinbefore.

Particular embodiments of the subject matter described in this specification can be implemented so as to realize one or more of the following advantages.

The segmentation system described in this specification can generate a large number of plausible segmentations of an image. By generating multiple possible segmentations of an image, the segmentation system models the inherent ambiguities present in segmenting the image. In one example, in medical imaging applications, a lesion might be visible in an image, but whether or not the lesion is malignant and the precise boundaries of the lesion may be ambiguous. In this example, the segmentation system may generate multiple different segmentations that each define respective boundaries of the lesion and respective predictions for whether the lesion is malignant. Diagnosis and treatment of patients may depend on segmentations of medical images (e.g., CT images). Providing only the most likely segmentation of a medical image may lead to misdiagnosis and sub-optimal treatment. The segmentation system described in this specification can provide multiple possible segmentations of a medical image that can be directly propagated into the next step in a diagnosis pipeline, used to suggest further diagnostic tests to resolve ambiguities, or provided to an expert for analysis, thereby potentially improving patient outcomes.

The segmentation system described in this specification may enable more efficient use of resources. For example, the segmentation system can facilitate more efficient resource usage by obviating the need for multiple people (e.g., physicians) to generate different manual segmentations of an image. As another example, rather than using different systems to generate multiple segmentations of an image from scratch (e.g., different neural network models), the system described in this specification can re-use the results of certain previous computations each time it generates a new segmentation of an image.

To generate a possible segmentation of an image, the segmentation system samples a latent variable from a latent space, and processes the latent variable and the image using a segmentation neural network. The system described in this specification can model the diversity and variations of possible image segmentations at various scales (e.g., spanning from the pixel level to the image level) by sampling latent variables from a "hierarchical" latent space that includes a hierarchy (sequence) of latent sub-spaces. The system can sample a respective latent sub-variable from each latent sub-space in accordance with a probability distribution over the latent sub-space that is generated based on: (i) the image, and (ii) latent sub-variables sampled from any preceding latent sub-spaces in the hierarchy. By sampling from a hierarchical latent space, the system can generate segmentations of an image that more accurately model complex variations in segmentation structures across scales.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
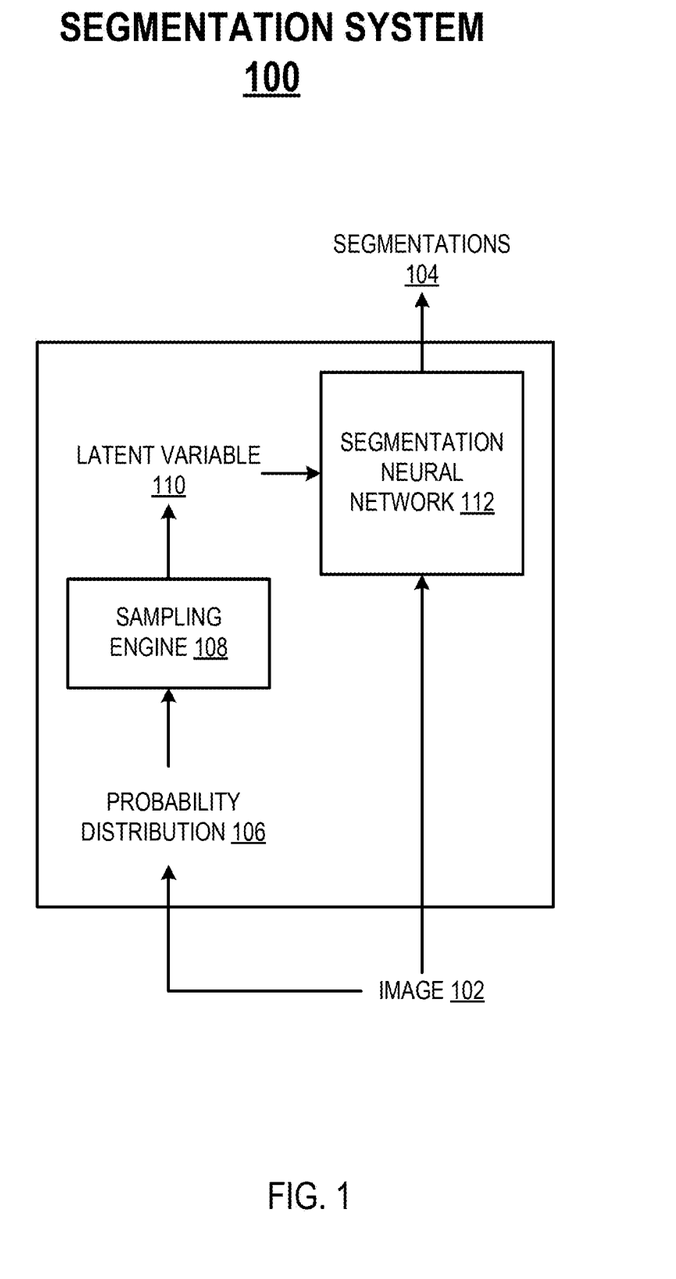
FIG. 1 shows an example segmentation system.

FIG. 1 shows an example segmentation system 100. The segmentation system 100 is an example of a system implemented as computer programs on one or more computers in one or more locations in which the systems, components, and techniques described below are implemented.

The segmentation system 100 is configured to process an image 102 to generate multiple possible segmentations 104 of the image 102, where each segmentation 104 represents a different hypothesis for the ground truth (i.e., actual) segmentation of the image 102.

The image 102 may be represented as an ordered collection of numerical values, e.g., as a one-dimensional (1-D), two-dimensional (2-D), three-dimensional (3-D), or N-dimensional (N-D) array of numerical values (where N is a positive integer value). As used throughout this specification, the components of an array of numerical values representing the image may be referred to as "pixels" or "voxels".

The image 102 may be captured using any appropriate imaging modality, e.g., a magnetic resonance imaging (MM) modality, a computed tomography (CT) imaging modality, a microscope imaging modality (e.g., a light microscope or electron microscope imaging modality), a photographic (camera) imaging modality, an optical coherence tomography (OCT) imaging modality, an ultrasound (US) imaging modality, or an X-ray imaging modality.

In some implementations, the image 102 may include multiple images that are each captured using a respective imaging modality. For example, the image 102 may include a concatenation of an MM image and a CT image (e.g., of the brain of a patient). In some implementations, the image 102 may include multiple images that are each captured at respective time points. For example, the image 102 may include a concatenation of MRI images (e.g., of the brain of a patient) that are each captured at a respective time point (e.g., such that the image 102 characterizes the progression of a disease in a patient).

Each segmentation 104 of the image 102 may be a "soft" segmentation that defines, for each pixel of the image 102, a respective score for each category in a predefined set of categories, where the score for a category characterizes a probability that the pixel is included in the category. Alternatively, each segmentation 104 of the image 102 may be a "hard" segmentation that specifies, for each pixel of the image 102, a corresponding category from the predefined set of categories. Generally, each segmentation 104 may be represented as an ordered collection of numerical values, e.g., an array of numerical values.

The segmentations 104 may segment the image 102 into any appropriate set of categories. For example, the image 102 may be a medical image (e.g., an Mll or CT image of a region of the body of a patient, or a microscope image of a fragment of tissue from a patient) and each category may represent a possible tissue type. In one example, the tissue types may include: "normal" tissue and "abnormal" (e.g., cancerous) tissue. In another example, each tissue type may specify a respective region of the body (e.g., bone tissue, heart tissue, liver tissue, lung tissue, etc.).

To generate a segmentation 104 of the image 102, the system 100 processes the image 102 to determine a probability distribution 106 over a latent space, and uses a sampling engine 108 to sample a latent variable 110 from the latent space in accordance with the probability distribution 106. The system 100 may process: (i) the image 102, and (ii) the sampled latent variable 110, using a segmentation neural network 112 to generate a segmentation 104 of the image 102.

Generally, the "latent space" may represent a collection of possible latent variables, and each latent variable may be represented as an ordered collection of one or more numerical values (e.g., a vector or matrix of numerical values). Each latent variable may specify a corresponding segmentation 104 of the image 102, and the system 100 may generate a probability distribution 106 over the latent space that assigns a higher probability to latent variables corresponding to more accurate segmentations of the image. To generate multiple segmentations 104 of the image 102, the system 100 may repeatedly sample latent variables 110 from the latent space, and generate a respective segmentation 104 corresponding to each sampled latent variable 110.

The system 100 can generate probability distributions 106 over the latent space and sample latent variables 110 in a variety of ways; a few examples are described in more detail next.

In one example, the system 100 may generate the latent variable by sampling from the latent space in accordance with a probability distribution over the latent space that depends on the image 102, but not on any portion of the latent variable itself. In this example, the latent variable may be referred to as a "global" latent variable obtained using a "global" sampling technique. An example implementation of the segmentation system 100 that samples global latent variables is described in more detail with reference to FIG. 2A-B.

In another example, the system may generate the latent variable by sequentially sampling a respective latent sub-variable from each latent sub-space in a sequence of latent sub-spaces in accordance with a respective probability distribution over each latent sub-space. The generated sequence of latent sub-variables collectively define the latent variable 110. As used throughout this specification, a "latent sub-space" may represent a collection of possible latent sub-variables, and each latent sub-variable may be represented as an ordered collection of one or more numerical values (e.g., a vector or matrix of numerical values). In this example, the latent variable may be referred to as a "hierarchical" latent variable obtained using a "hierarchical" sampling technique. An example implementation of the segmentation system 100 that samples hierarchical latent variables is described in more detail with reference to FIG. 3A-B.

The system 100 may generate the probability distribution over each latent sub-space based on: (i) the image 102, and (ii) latent sub-variables sampled from preceding latent sub-spaces (i.e., that precede the latent sub-space in the sequence of latent sub-spaces). For example, the system 100 may generate a probability distribution over the first latent sub-space (i.e., in the sequence of latent sub-spaces) as an output of one or more neural network layers that process the image 102 (or feature maps corresponding to the image 102). For each subsequent latent sub-space, the system 100 may generate a probability distribution over the latent sub-space as an output of one or more neural network layers that process: (i) the image 102 (or feature maps corresponding to the image 102), and (ii) respective latent sub-variables sampled from preceding latent sub-spaces.

As used throughout this specification, a feature map corresponding to the image 102 may refer to an output generated by processing the image 102 using one or more neural network layers. For example, a feature map corresponding to the image 102 may be generated as an intermediate output of the segmentation neural network by processing the image 102. An intermediate output of the segmentation neural network 112 may refer to an output generated by one or more intermediate (hidden) layers of the segmentation neural network.

Optionally, the sequence of latent sub-spaces may be a sequence of increasing dimensionality, i.e., such that the dimensionality of each latent sub-space is greater than the dimensionality of the preceding latent sub-space. Latent variables sampled from latent sub-spaces with lower dimensionalities may implicitly characterize global features relevant to the segmentation as a whole, e.g., the predisposition of a patient for a certain disease. Latent variables sampled from latent sub-spaces with higher dimensionalities may implicitly characterize local features relevant to specific parts of the segmentation, e.g., whether a particular nodule is cancerous, or the position of the boundary of a particular nodule.

The segmentation neural network 112 can have any appropriate neural network architecture that enables it to perform its described functions, in particular, processing an image 102 and a latent variable 110 to generate a corresponding segmentation 104 of the image 102. For example, the segmentation neural network 112 may have a convolutional neural network architecture that includes one or more convolutional neural network layers. Example architectures of the segmentation neural network 112 are described in more detail below with reference to FIG. 2A-B and FIG. 3A-B.

Figure 2A:
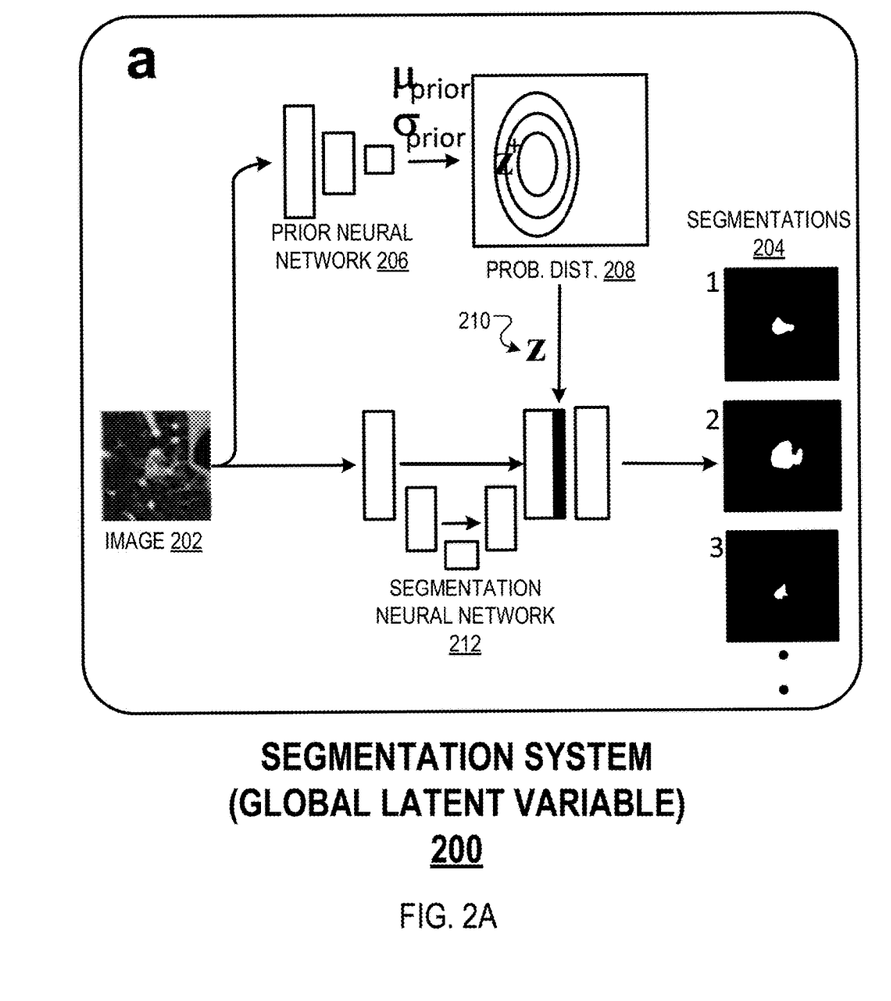
FIG. 2A shows an example segmentation system that uses a global sampling technique for sampling latent variables.

FIG. 2A shows an example segmentation system 200, which is an example implementation of the segmentation system 100 (described with reference to FIG. 1) that uses a global sampling technique for sampling latent variables. The segmentation system 200 is an example of a system implemented as computer programs on one or more computers in one or more locations in which the systems, components, and techniques described below are implemented.

The segmentation system 200 is configured to process an image 202 to generate multiple segmentations 204 of the image 202, where each segmentation is specified by a latent variable sampled from a latent space in accordance with a global sampling technique.

To generate a segmentation 204, the system 200 may process the image 202 using a prior neural network 206 to generate an output that defines the parameters of a probability distribution 208 over the latent space. In one example, the latent space may be an N-dimensional Euclidean space (i.e., $\mathbb{R}^N$) and the probability distribution over the latent space may be a Normal probability distribution specified by a mean vector $\mu_{prior}$ and a covariance matrix (or covariance vector) $\sigma_{prior}$.

The prior neural network 206 may have any appropriate neural network architecture that enables it to perform its described function. For example, the prior neural network 206 may have a convolutional neural network architecture that includes an input layer, one or more intermediate (i.e., hidden) convolutional neural network layers, and a fully-connected output layer.

The system 200 samples a latent variable 210 from the latent space in accordance with the probability distribution 208 over the latent space, and provides an input including: (i) the image 202, and (ii) the sampled latent variable 210, to the segmentation neural network 212. The segmentation neural network 212 is configured to process the input to generate a corresponding segmentation 204 of the image 202.

The segmentation neural network 212 may have any appropriate neural network architecture that enables it to perform its described function. For example, the segmentation neural network may include: (i) a feature extraction sub-network, and (ii) a prediction sub-network. (As used throughout this specification, a "sub-network" of a neural network refers to a group of one or more layers of the neural network).

The feature extraction sub-network of the segmentation neural network 212 may be configured to process the image 202 to generate a feature map characterizing the image 202. The feature map may be represented, e.g., as an array of numerical values having one or more "spatial" dimensions and a "channel" dimension. The feature extraction sub-network may have any appropriate neural network architecture, e.g., a convolutional neural network architecture including one or more convolutional neural network layers. In a particular example, the feature extraction sub-network may have the U-Net neural network architecture described with reference to: O. Ronneberger et al., "U-Net: Convolutional Networks for Biomedical Image Segmentation", arXiv: 1505.04597.

The prediction sub-network may be configured to combine the feature map (i.e., generated by the feature extraction sub-network) and the latent variable 210, and to process the combination of the feature map and the latent variable 210 to generate the segmentation 204. The prediction sub-network may combine the feature map and the latent variable, e.g., by "broadcasting" (i.e., concatenating) the latent variable along the spatial dimensions of the feature map. The prediction sub-network may have a neural network architecture that includes one or more 1×1 convolutional neural network layers, i.e., convolutional layers with 1×1-dimensional kernels.

To generate multiple segmentations 204 of the image 202, the system 200 can sample multiple latent variables from the latent space, i.e., in accordance with the probability distribution over the latent space generated by the prior neural network 206. The system 200 may avoid regenerating the parameters of the probability distribution over the latent space each time a latent variable is sampled, e.g., by generating the probability distribution parameters only once, and thereafter storing and reusing them. Similarly, the system 200 may avoid regenerating the feature map output by the feature extraction sub-network of the segmentation neural network 212 each time a latent variable is sampled, e.g., by generating the feature map only once, and thereafter storing and reusing it.

Figure 2B:
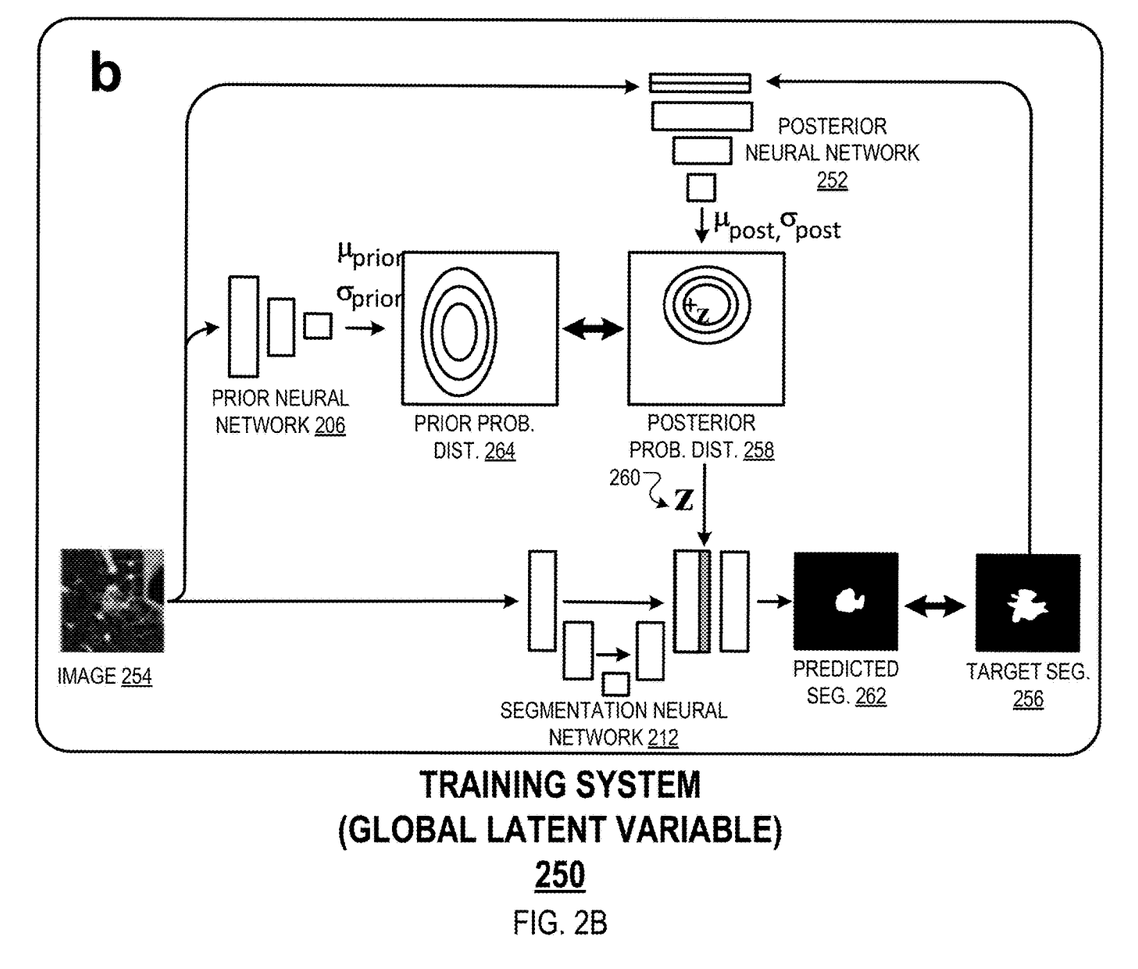
FIG. 2B shows an example training system for training a segmentation system that uses a global sampling technique for sampling latent variables.

FIG. 2B shows an example training system 250 for training a segmentation system that uses a global sampling technique for sampling latent variables, e.g., the segmentation system 200 described with reference to FIG. 2A. The training system 250 is an example of a system implemented as computer programs on one or more computers in one or more locations in which the systems, components, and techniques described below are implemented.

The training system 250 is configured to train the segmentation system by jointly training the prior neural network 206 and the segmentation neural network 212 (i.e., described with reference to FIG. 2A) along with a posterior neural network 252 on a set of training data. The posterior neural network 252 (which will be described in more detail below) facilitates training the segmentation system to generate probability distributions over the latent space that assign a higher probability to latent variables corresponding to more accurate segmentations of input images.

The training data may include multiple training examples, where each training example includes: (i) a training image, and (ii) a target segmentation of the training image. Each target segmentation may be manually generated, e.g., by a human expert. To enable the segmentation system to learn a range of variations among plausible segmentations of a training image, the training data may include multiple training examples having the same training image but different target segmentations, e.g., that are generated by different human experts.

The posterior neural network 252 is configured to process: (i) a training image 254, and (ii) a target segmentation 256 of the training image 254, to generate an output that defines the parameters of a "posterior" probability distribution 258 over the latent space. In one example, the latent space may be an N-dimensional Euclidean space (i.e., $\mathbb{R}^N$) and the posterior probability distribution may be a Normal (i.e., Gaussian) probability distribution specified by a mean vector $\mu_{post}$ and a covariance matrix (or covariance vector) $\sigma_{post}$.

The posterior neural network 252 may have any appropriate neural network architecture that enables it to perform its described function. For example, the posterior neural network 252 may have a convolutional neural network architecture that includes an input layer, one or more intermediate (i.e., hidden) convolutional neural network layers, and a fully-connected output layer.

At each of multiple training iterations, the training system 250 obtains a batch of training examples, e.g., by sampling one or more training examples from the training data. For each training example, the training system 250 processes the training image 254 and target segmentation 256 specified by the training example using the posterior neural network 252 to generate a corresponding posterior probability distribution 258 over the latent space. The training system 250 samples a latent variable 260 from the latent space in accordance with the posterior probability distribution 258 generated for the training example, and processes the training image 254 and the sampled latent variable 260 using the segmentation neural network 212 to generate a predicted segmentation 262. The training system 250 also processes the training image 254 specified by the training example using the prior neural network 206 to generate a "prior" probability distribution 264 over the latent space.

The training system 250 then jointly optimizes the parameters of the prior neural network 206, the segmentation neural network 212, and the posterior neural network 252 to optimize an objective function, e.g., using gradient descent. The objective function $\mathcal{L}$ (evaluated for a given training example) may be given by:

$$\mathcal{L} = Err(Y,\hat{Y}) - \beta \cdot D(P,Q) \quad (1)$$

where $Err(Y,\hat{Y})$ denotes an error (e.g., a cross entropy error) between the target segmentation Y 256 and the predicted segmentation $\hat{Y}$ 262 (i.e., that is generated by processing a latent variable sampled in accordance with the posterior probability distribution), $\beta$ is a constant factor, and $D(P,Q)$ represents an error (e.g., a Kullback-Leibler divergence) between the prior probability distribution P 264 and the posterior probability distribution Q 258 for the training example. Optimizing the objective function in equation (1) encourages the prior probability distribution 264 to match the posterior probability distribution 258, and encourages the predicted segmentation 262 corresponding to a latent variable sampled in accordance with the posterior distribution 258 to match the target segmentation 256. The objective function given by equation (1) is provided for illustrative purposes only; other objective functions are possible.

Figure 3A:
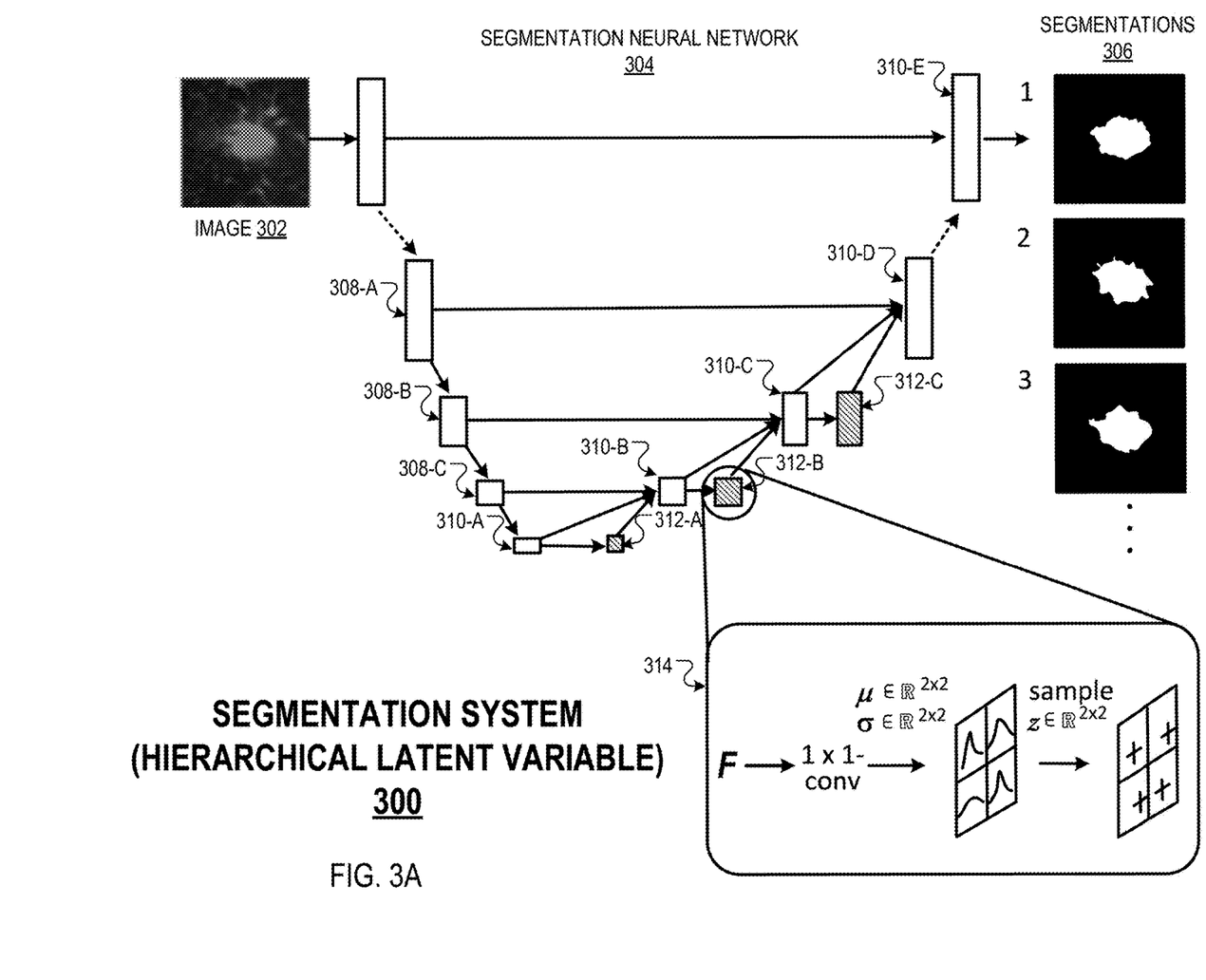
FIG. 3A shows an example segmentation system, which is an example implementation of a segmentation system that uses a hierarchical sampling technique for sampling latent variables.

FIG. 3A shows an example segmentation system 300, which is an example implementation of a segmentation system 100 (described with reference to FIG. 1) that uses a hierarchical sampling technique for sampling latent variables. The segmentation system 300 is an example of a system implemented as computer programs on one or more computers in one or more locations in which the systems, components, and techniques described below are implemented.

The segmentation system 300 is configured to process an image 302 using a segmentation neural network 304 to generate multiple segmentations 306 of the image 302, where each segmentation is specified by a latent variable sampled from a latent space in accordance with a hierarchical sampling technique. To sample a latent variable, the system 300 may sample a respective latent sub-variable from each latent sub-space in a sequence of latent sub-spaces in accordance with a probability distribution over each latent sub-space, and the generated sequence of latent sub-variables may collectively define the latent variable.

The segmentation neural network 304 includes a sequence of one or more "encoder" blocks, e.g., 308-A-C, a sequence of one or more "decoder" blocks, e.g., 310-A-E, and one or more "prior" blocks, e.g., 312-A-C. A "block" refers to a group of one or more neural network layers. Generally, the input to a block and the output of a block may be represented as respective arrays of numerical values that are indexed along one or more "spatial" dimensions (e.g., x-y dimensions, or x-y-z dimensions) and a "channel" dimension. The "resolution" of a block input/output along a dimension refers to the number of index values along that dimension.

Each encoder block is configured to process an encoder block input to generate an encoder block output having a lower spatial resolution than the encoder block input, i.e., such that the resolution of the encoder block output is less than the resolution of the encoder block input along at least one spatial dimension. The first encoder block may process the image 302, and each subsequent encoder block may process a feature map output by the preceding encoder block.

Each decoder block is configured to process a decoder block input to generate a decoder block output having a higher spatial resolution than the decoder block input, i.e., such that the resolution of the decoder block output is greater than the resolution of the decoder block input along at least one spatial dimension. The first decoder block in the segmentation neural network 304 may process an input including the output of a corresponding encoder block, and each subsequent decoder block may process an input including: (i) the output of a corresponding encoder block, and (ii) the output of the preceding decoder block.

Each prior block corresponds to a respective decoder block, and is configured to process a feature map generated by the corresponding decoder block to generate an output that defines the parameters of a probability distribution over a corresponding latent sub-space. The latent sub-space may be a space of arrays of numerical values having the same spatial resolution as the feature map generated by the corresponding decoder block. For example, as illustrated by 314, the prior block 312-B may process a feature map $F \in \mathbb{R}^{2 \times 2 \times C}$ (i.e., having spatial resolution 2×2 and channel resolution C) by one or more 1×1 convolutional neural network layers to generate the parameters of a Normal probability distribution over $\mathbb{R}^{2 \times 2}$, where $\mu \in \mathbb{R}^{2 \times 2}$ is an array of mean parameters and $\sigma \in \mathbb{R}^{2 \times 2}$ is an array of standard deviation parameters. The system 300 may then sample a latent sub-variable $z \in^{2 \times 2}$ in accordance with the probability distribution parameters ($\mu$, $\sigma$).

After generating the parameters of a probability distribution over a latent sub-space corresponding to a decoder block, the system 300 may sample a latent sub-variable from the latent sub-space and provide the latent sub-variable as an input to the next decoder block (i.e., in the sequence of decoder blocks). For example, the system 300 may concatenate the latent sub-variable to the other inputs to the next decoder block along their respective spatial dimensions. In some cases, the latent sub-variable may have a lower spatial resolution than the decoder block output, and the system 300 may up-scale the latent sub-variable to have the same spatial resolution as the other inputs to the next decoder block. Up-scaling the latent sub-variable may refer to mapping the array of numerical values representing the latent sub-variable to another array of numerical values having a higher spatial resolution, e.g., where some data values in the up-scaled array may be interpolated between data values in the original array. It can be appreciated that the sampled sequence of latent sub-variables may be a sequence of arrays of numerical values of increasing spatial resolution, i.e., such that the spatial resolution of each latent sub-variable is greater than the spatial resolution of the preceding latent sub-variable.

The final decoder block of the segmentation neural network 304 may generate an output that includes the segmentation 306 of the input image 302. Each time the system 300 processes an image 302 using the segmentation neural network 304, a different sequence of latent sub-variables may be sampled from the respective latent sub-spaces and a different segmentation 306 of the image 302 may be generated. The system 300 may avoid regenerating the feature maps generated by the encoder blocks each time the same image 302 is processed, e.g., by generating these feature maps only once, and thereafter storing and reusing them each time the same image is processed.

Generating latent sub-variables represented as arrays of numerical values having the same spatial resolution as the feature maps generated by corresponding decoder blocks (as described above) endows the latent sub-variables with spatial structure. The spatial structure of the latent sub-variables can improve the capacity of the system 300 to model independent local variations, e.g., the presence of multiple lesions.

In some implementations, the segmentation neural network 304 includes a respective prior block corresponding to each decoder block, while in other implementations, the segmentation neural network 304 includes a respective prior block corresponding to only a proper subset of the decoder blocks.

In some implementations, the segmentation neural network 304 may be implemented as a fully-convolutional neural network, i.e., where each layer is a convolutional layer. In these implementations, the segmentation neural network 304 may process images having arbitrary spatial resolutions, and the spatial resolutions of the inputs/outputs of the neural network blocks may vary (e.g., proportionally) based on the spatial resolution of the image being processed. In particular, the spatial resolutions of the latent sub-variables (which may be directly linked to the spatial resolutions of the feature maps generated by the decoder blocks) may vary based on the spatial resolution of the image being processed. For example, the system 300 may sample latent sub-variables with higher spatial resolutions when processing an image with a higher spatial resolution, which can enable the system 300 to more effectively capture the greater range of possible variations in segmentations of images with higher spatial resolutions.

Figure 3B:
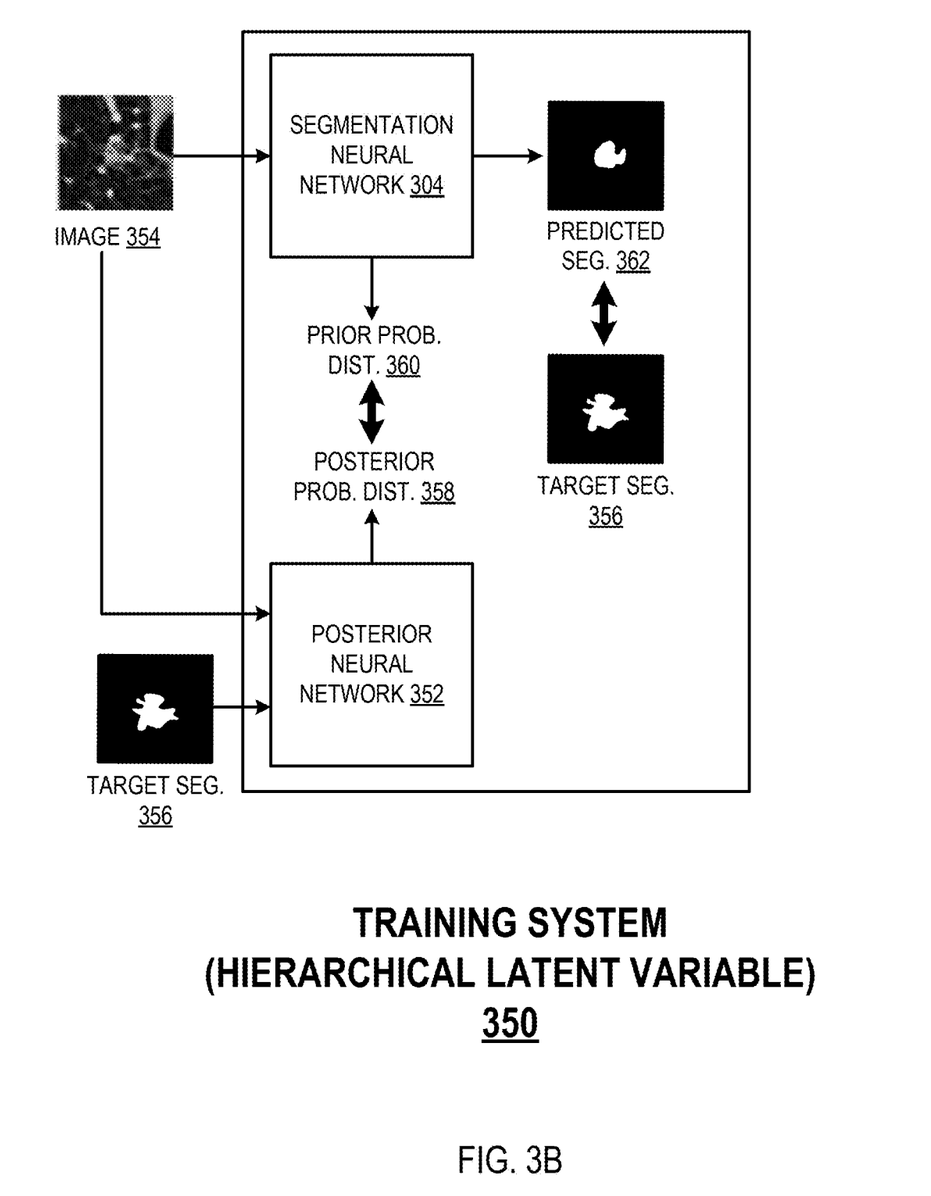
FIG. 3B shows an example training system for training a segmentation system that uses a hierarchical sampling technique for sampling latent variables.

FIG. 3B shows an example training system 350 for training a segmentation system that uses a hierarchical sampling technique for sampling latent variables, e.g., the segmentation system 300 described with reference to FIG. 3A. The training system 350 is an example of a system implemented as computer programs on one or more computers in one or more locations in which the systems, components, and techniques described below are implemented.

The training system 350 is configured to train the segmentation system by jointly training the segmentation neural network 304 (i.e., described with reference to FIG. 3A) and a posterior neural network 352 on a set of training data. The posterior neural network 352 (which will be described in more detail below) facilitates training the segmentation neural network 304 to generate probability distributions over the latent sub-spaces that assign higher probabilities to sub-latent variables corresponding to more accurate segmentations of input images.

The training data may include multiple training examples, where each training example includes: (i) a training image, and (ii) a target segmentation of the training image. Each target segmentation may be manually generated, e.g., by a human expert. To enable the segmentation system to learn a range of variations among plausible segmentations of a training image, the training data may include multiple training examples having the same training image but different target segmentations, e.g., that are generated by different human experts.

The posterior neural network 352 is configured to process: (i) a training image 354, and (ii) a target segmentation 356 of the training image 354, to generate an output that defines the parameters of a respective "posterior" probability distribution 358 over each latent sub-space in the sequence of latent sub-spaces. In one example, each latent sub-space may be a space of arrays of numerical values having a respective spatial resolution and the posterior probability distribution may be a Normal probability distribution specified by an array of mean parameters and an array of standard deviation parameters.

The posterior neural network 352 may have any appropriate neural network architecture that enables it to perform its described function. For example, the posterior neural network 352 may have an architecture that substantially matches the architecture of the segmentation neural network 304, e.g., with a sequence of encoder blocks, a sequence of decoder blocks, and one or more "posterior" blocks (i.e., corresponding to the prior blocks of the prior neural network). Each posterior block may be configured to process a feature map generated by a corresponding decoder block of the posterior neural network to generate an output that defines the parameters of a posterior probability distribution over a corresponding latent sub-space. In contrast to the segmentation neural network 304, the posterior neural network 352 may exclude the final decoder block of the segmentation neural network 304, i.e., that generates the predicted segmentation. The dimensionalities of the inputs/outputs of the blocks of the posterior neural network 352 may also differ from the segmentation neural network 304, e.g., because the posterior neural network 352 also processes the target segmentation 356 in addition to the training image 354.

At each of multiple training iterations, the training system 350 obtains a batch of one or more training examples, and provides the training image 354 and target segmentation 356 specified by each training example as inputs to the posterior neural network 352. For each training example, the training system 350 processes the training image 354 and the target segmentation 356 using the posterior neural network 352 to generate a respective posterior probability distribution 358 over each latent sub-space. The training system 350 also processes the training image 354 using the segmentation neural network 304 to generate a respective prior probability distribution 360 over each latent sub-space and a predicted segmentation 362 of the training image 354. To generate the predicted segmentation 362, the segmentation neural network 304 processes a respective latent variable sampled from each latent sub-space in accordance with the posterior probability distribution 358 over the sub-space (i.e., rather than latent sub-variables sampled in accordance with the prior probability distributions 360).

The training system 350 then jointly optimizes the parameters of the segmentation neural network 304 and the posterior neural network 352 to optimize an objective function, e.g., using gradient descent. The objective function $\mathcal{L}$ (evaluated for a given training example) may be given by:

$$\mathcal{L} = Err(Y, \hat{Y}) - \beta \cdot \sum_{i=1}^{L} D(P_i, Q_i) \qquad (2)$$

where $Err(Y, \hat{Y})$ denotes an error (e.g., a cross entropy error) between the target segmentation Y and the predicted segmentation $\hat{Y}$ (i.e., that is generated by processing latent sub-variables sampled in accordance with the posterior probability distributions), $\beta$ is a constant factor, i indexes the latent sub-spaces, L is the number of latent sub-spaces, and $D(P_i, Q_i)$ represents an error (e.g., a Kullback-Leibler divergence) between the prior probability distribution $P_i$ and the posterior probability distribution $Q_i$ over the i-th latent sub-space. Optimizing the objective function in equation (2) encourages the prior probability distributions to match the posterior probability distributions, and encourages the predicted segmentation corresponding to latent sub-variables sampled in accordance with the posterior distributions to match the target segmentation. The objective function in equation (2) is provided for illustrative purposes only, and other objective functions are possible.

Figure 4:
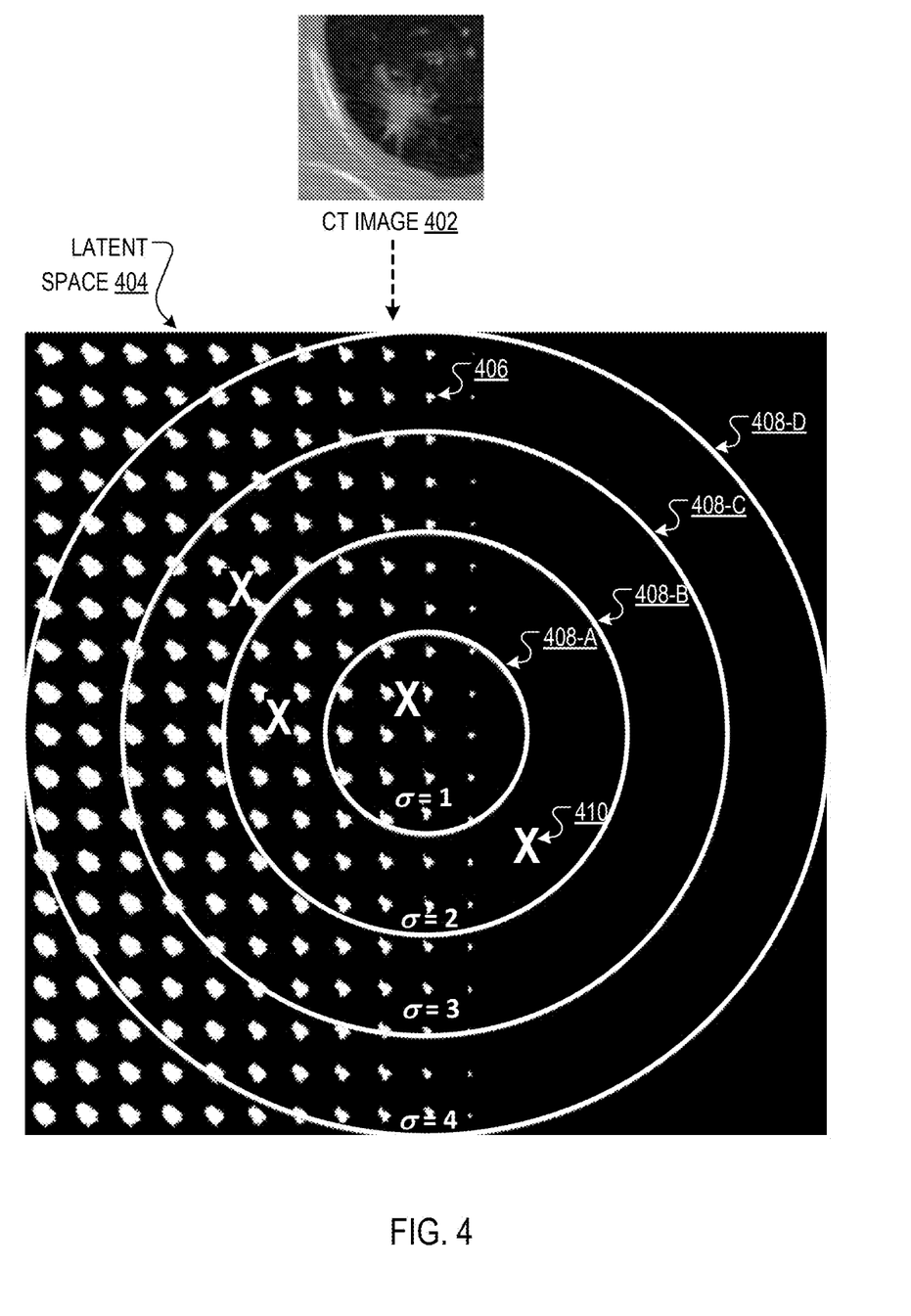
FIG. 4 shows a CT image of a portion of a lung and an illustration of a corresponding latent space.

FIG. 4 shows a CT image 402 of a portion of a lung and an illustration of a (2-D) latent space 404. For each of multiple positions in the latent space 404, a segmentation (e.g., 406) of a region of abnormal tissue in the CT image 402 that is generated by a segmentation neural network by processing the latent variable at the position in the latent space is overlaid on the latent space 404. For ease of presentation, the latent space 404 has been rescaled so that the prior probability distribution over the latent space is a unit Normal distribution, and the circles 408-A-D denote deviations from the mean of the prior probability distribution in integer multiples of the standard deviation a. The white Xs (e.g., 410) overlaid on the latent space 404 denote the positions in the latent space 404 corresponding to target segmentations of the abnormal tissue in the CT image 402 that were manually generated by different human experts.

Figure 5:
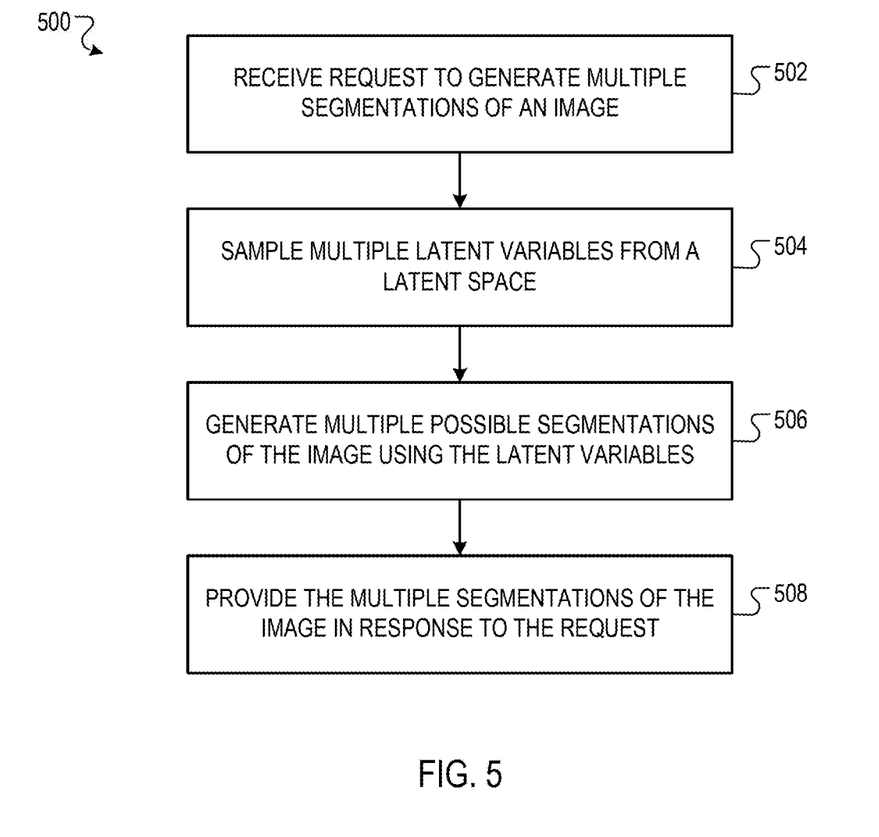
FIG. 5 is a flow diagram of an example process for generating multiple possible segmentations of an image.

FIG. 5 is a flow diagram of an example process 500 for generating multiple possible segmentations of an image. For convenience, the process 500 will be described as being performed by a system of one or more computers located in one or more locations. For example, a segmentation system, e.g., the segmentation system 100 of FIG. 1, appropriately programmed in accordance with this specification, can perform the process 500.

The system receives a request to generate multiple segmentations of an image (502).

The system samples multiple latent variables from a latent space, where each latent variable is sampled from the latent space in accordance with a respective probability distribution over the latent space that is determined based on (at least) the image (504).

In some implementations, the system samples each latent variable using a global sampling technique. In these implementations, the system samples each latent variable in accordance with a respective probability distribution over the latent space that depends on the image, but not on any portion of the latent variable itself.

In some implementations, the system samples each latent variable using a hierarchical sampling technique. In these implementations, the latent space includes a hierarchy (sequence) of latent subspaces, and sampling a latent variable from the latent space includes sequentially sampling a respective latent sub-variable from each latent sub-space of the latent space. To sample a latent sub-variable from a given latent sub-space, the system may generate a probability distribution over the given latent sub-space based on: (i) the image, and (ii) latent sub-variables sampled from any latent sub-spaces that precede the given latent sub-space in the hierarchy of latent sub-spaces. The system may then sample the latent sub-variable from the given latent sub-space in accordance with the probability distribution over the given latent sub-space.

The system generates multiple possible segmentations of the image (506). In particular, for each latent variable, the system processes the image and the latent variable using a segmentation neural network having a set of segmentation neural network parameters to generate the possible segmentation of the image.

The system provides the multiple segmentations of the image in response to the request (508).

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more data processing apparatus, the method comprising:
   receiving a request to generate a plurality of possible segmentations of an image;
   sampling a plurality of latent variables from a latent space, wherein each latent variable is sampled from the latent space in accordance with a respective probability distribution over the latent space that is determined based on the image;
   generating a plurality of possible segmentations of the image, comprising, for each latent variable, processing the image and the latent variable using a segmentation neural network having a plurality of segmentation neural network parameters to generate the possible segmentation of the image; and
   providing the plurality of possible segmentations of the image in response to the request.

2. The method of claim 1, wherein sampling the plurality of latent variables from the latent space comprises:
   generating a probability distribution over the latent space based on the image; and
   sampling each of the plurality of latent variables from the latent space in accordance with the probability distribution.

3. The method of claim 2, wherein generating a probability distribution over the latent space based on the image comprises:
   processing the image using a prior neural network to generate an output that defines parameters of the probability distribution over the latent space.

4. The method of claim 3, wherein the probability distribution is a Normal probability distribution, and the parameters of the probability distribution include a mean vector and a variance vector.

5. The method of claim 3, wherein the segmentation neural network and the prior neural network have been trained jointly with a posterior neural network configured to, during training, process a training image and a target segmentation of the training image to generate an output that defines parameters of a posterior probability distribution over the latent space.

6. The method of claim 1, wherein processing the image and the latent variable using a segmentation neural network to generate the possible segmentation of the image comprises:
   processing the image using a first plurality of segmentation neural network layers to generate a feature map; and
   processing the feature map and the latent variable using a second plurality of segmentation neural network layers to generate the possible segmentation of the image.

7. The method of claim 1, wherein:
   the latent space comprises a hierarchy of latent sub-spaces; and
   sampling a latent variable from the latent space comprises sampling a respective latent sub-variable from each latent sub-space of the latent space, wherein sampling a latent sub-variable from a given latent sub-space comprises:
      generating a probability distribution over the given latent sub-space based on: (i) the image, and (ii) latent sub-variables sampled from any latent sub-spaces that precede the given latent sub-space in the hierarchy of latent sub-spaces; and
      sampling the latent sub-variable from the given latent sub-space in accordance with the probability distribution over the given latent sub-space.

8. The method of claim 7, wherein for each particular latent sub-space in the hierarchy of latent subspaces, a dimensionality of the particular latent sub-space is greater than a dimensionality of any latent sub-space that precedes the particular latent sub-space in the hierarchy of latent sub-spaces.

9. The method of claim 7, wherein for each latent sub-space:
   the latent sub-space comprises a space of arrays of numerical values having a respective spatial resolution corresponding to the latent sub-space; and
   the spatial resolution corresponding to the latent sub-space is greater than a spatial resolution corresponding to any preceding latent sub-spaces.

10. The method of claim 9, wherein the spatial resolution corresponding to each latent sub-space depends on a spatial resolution of the image.

11. The method of claim 7, wherein generating the probability distribution over the first latent sub-space in the hierarchy of latent sub-spaces comprises:
    processing one or more feature maps derived from the image using one or more neural network layers to generate an output that defines parameters of the probability distribution over the first latent sub-space.

12. The method of claim 11, wherein the one or more feature maps are intermediate outputs of the segmentation neural network.

13. The method of claim 11, wherein the one or more neural network layers are intermediate layers of the segmentation neural network.

14. The method of claim 11, wherein the probability distribution over the first latent sub-space is a Normal probability distribution, and the parameters of the probability distribution over the first latent sub-space include a mean vector and a variance vector.

15. The method of claim 7, wherein generating the probability distribution over each latent sub-space after the first latent sub-space in the hierarchy of latent sub-spaces comprises:
processing one or more feature maps derived from the image and a representation of the latent sub-variable sampled from the preceding latent sub-space in the hierarchy of latent sub-spaces using one or more neural network layers to generate an output that defines parameters of the probability distribution over the latent sub-space.

16. The method of claim 15, wherein the representation of the latent sub-variable sampled from the preceding latent sub-space is an up-scaled representation of the latent sub-variable sampled from the preceding latent sub-space.

17. The method of claim 15, wherein the one or more feature maps are intermediate outputs of the segmentation neural network.

18. The method of claim 15, wherein the one or more neural network layers are intermediate layers of the segmentation neural network.

19. The method of claim 15, wherein for each latent sub-space after the first latent sub-space, the probability distribution over the latent sub-space is a Normal probability distribution, and the parameters of the probability distribution over the latent sub-space include a mean vector and a variance vector.

20. The method of claim 7, wherein processing the image and the latent variable using a segmentation neural network to generate the possible segmentation of the image comprises:
providing the image as an input to an input layer of the segmentation neural network; and
providing each latent sub-variable as an input to a respective intermediate layer of the segmentation neural network.

21. The method of claim 7, wherein the segmentation neural network has been trained jointly with a posterior neural network configured to, during training, process a training image and a target segmentation of the training image to generate an output that defines, for each latent sub-space of the hierarchy of latent sub-spaces, parameters of a posterior probability distribution over the latent sub-space.

22. The method of claim 1, wherein each possible segmentation of the image characterizes, for each pixel of the image, a respective likelihood that the pixel is included in each of a plurality of categories.

23. The method of claim 22, wherein the image is a medical image and each of the plurality of categories corresponds to a respective tissue type.

24. The method of claim 23, wherein the medical image is a computed tomography (CT) image.

25. The method of claim 1, wherein the segmentation neural network is a convolutional neural network.

26. The method of claim 25, wherein the segmentation neural network has a U-Net neural network architecture.

27. A system comprising one or more computers and one or more storage devices storing instructions that when executed by the one or more computers cause the one or more computers to perform operations comprising:
receiving a request to generate a plurality of possible segmentations of an image;
sampling a plurality of latent variables from a latent space, wherein each latent variable is sampled from the latent space in accordance with a respective probability distribution over the latent space that is determined based on the image;
generating a plurality of possible segmentations of the image, comprising, for each latent variable, processing the image and the latent variable using a segmentation neural network having a plurality of segmentation neural network parameters to generate the possible segmentation of the image; and
providing the plurality of possible segmentations of the image in response to the request.

28. One or more non-transitory computer storage media storing instructions that when executed by one or more computers cause the one or more computers to perform operations comprising:
receiving a request to generate a plurality of possible segmentations of an image;
sampling a plurality of latent variables from a latent space, wherein each latent variable is sampled from the latent space in accordance with a respective probability distribution over the latent space that is determined based on the image;
generating a plurality of possible segmentations of the image, comprising, for each latent variable, processing the image and the latent variable using a segmentation neural network having a plurality of segmentation neural network parameters to generate the possible segmentation of the image; and
providing the plurality of possible segmentations of the image in response to the request.

* * * * *